US005858336A

United States Patent [19]
Graf et al.

[11] Patent Number: 5,858,336
[45] Date of Patent: Jan. 12, 1999

[54] CLEAR STICK DEODORANT

[75] Inventors: Jeffrey S. Graf, Ridgewood; Ronald Matesevac, Teaneck, both of N.J.; Philip Franco, Warwick, N.Y.

[73] Assignee: Avon Products, Inc., New York, N.Y.

[21] Appl. No.: 949,219

[22] Filed: Oct. 10, 1997

[51] Int. Cl.$^6$ ............................... A61K 7/32; A61K 7/00
[52] U.S. Cl. ................... 424/65; 424/78.02; 424/78.08; 424/78.18; 424/401
[58] Field of Search .................. 424/401, 65, 78.02, 424/78.08, 78.18

[56] References Cited

U.S. PATENT DOCUMENTS

| | | | |
|---|---|---|---|
| 3,943,242 | 3/1976 | Fogel et al. | 424/65 |
| 4,011,311 | 3/1977 | Noomen et al. | 424/65 |
| 4,117,110 | 9/1978 | Hautmann | 424/76 |
| 4,120,948 | 10/1978 | Shelton | 424/66 |
| 4,202,879 | 5/1980 | Shelton | 424/66 |
| 4,252,789 | 2/1981 | Broad | 424/65 |
| 4,278,658 | 7/1981 | Hooper et al. | 424/65 |
| 4,280,994 | 7/1981 | Turney | 424/68 |
| 4,305,930 | 12/1981 | Lewis | 424/65 |
| 4,369,173 | 1/1983 | Causland et al. | 424/35 |
| 4,431,837 | 2/1984 | Geria | 560/112 |
| 4,440,741 | 4/1984 | Marschner | 424/65 |
| 4,440,742 | 4/1984 | Marschner | 424/65 |
| 4,478,853 | 10/1984 | Chaussee | 424/358 |
| 4,504,465 | 3/1985 | Sampson et al. | 424/65 |
| 4,524,062 | 6/1985 | Laba et al. | 424/65 |
| 4,617,185 | 10/1986 | DiPietro | 424/65 |
| 4,673,570 | 6/1987 | Soldati | 424/66 |
| 4,702,916 | 10/1987 | Geria | 424/400 |
| 4,743,444 | 5/1988 | McCall | 424/65 |
| 4,759,924 | 7/1988 | Luebbe et al. | 424/42 |
| 4,816,261 | 3/1989 | Luebbe et al. | 424/65 |
| 4,822,602 | 4/1989 | Sabatelli | 424/65 |
| 4,906,454 | 3/1990 | Melanson, Jr. et al. | 424/47 |
| 4,944,937 | 7/1990 | McCall | 424/65 |
| 4,970,220 | 11/1990 | Chaussee | 514/358 |
| 5,114,717 | 5/1992 | Kuznitz et al. | 424/401 |
| 5,120,541 | 6/1992 | Macaulay et al. | 424/401 |
| 5,128,123 | 7/1992 | Brewster et al. | 424/65 |
| 5,182,103 | 1/1993 | Nakane et al. | 424/78.03 |
| 5,198,218 | 3/1993 | Kuznitz et al. | 424/401 |
| 5,270,034 | 12/1993 | Cheng | 424/68 |
| 5,284,649 | 2/1994 | Juneja | 424/67 |
| 5,316,761 | 5/1994 | Brazinsky | 424/65 |
| 5,368,848 | 11/1994 | Brazinsky et al. | 424/65 |
| 5,376,363 | 12/1994 | Benfatto et al. | 424/66 |
| 5,378,468 | 1/1995 | Suffis et al. | 424/401 |
| 5,405,605 | 4/1995 | Shin | 424/68 |
| 5,407,668 | 4/1995 | Kellner | 424/65 |
| 5,417,876 | 5/1995 | Tokosh et al. | 252/108 |
| 5,417,962 | 5/1995 | Brodowski et al. | 424/65 |
| 5,424,070 | 6/1995 | Kasat et al. | 424/401 |
| 5,458,880 | 10/1995 | Kasat et al. | 424/401 |
| 5,462,736 | 10/1995 | Rech et al. | 424/401 |
| 5,474,778 | 12/1995 | Ichikawa et al. | 424/401 |
| 5,484,597 | 1/1996 | Slavtcheff et al. | 424/401 |
| 5,520,907 | 5/1996 | Orofino et al. | 424/65 |
| 5,603,925 | 2/1997 | Ross et al. | 424/65 |
| 5,626,852 | 5/1997 | Suffis et al. | 424/401 |
| 5,639,463 | 6/1997 | Kilpatrick-Liverman | 424/401 |

FOREIGN PATENT DOCUMENTS

| | | |
|---|---|---|
| 0 450 597 A2 | 4/1991 | European Pat. Off. |
| 92 03895 | 3/1992 | France |

OTHER PUBLICATIONS

Cosmetics and the Skin, Wells et al., 1964, pp. 351, 352, 356
Cosmetics Science and Technology, Second Edition, vol. 2, Balsam et al., eds., 1972, pp. 407–409.
The Chemistry and Manufacture of Cosmetics, Second Edition, vol. III, deNavarre, 1975, two pages thereof.
Cosmetics and Toiletries, vol. 92, Jul. 1977, pp. 64 and 73–75.
Cosmetics and Toiletries, vol. 95, Jul. 1980, p. 59
Cosmetics, Fragrances and Flavors, Louis Appell, 1982, pp. 55, 62 and 63.

*Primary Examiner*—Alan L. Rotman
*Assistant Examiner*—Charanjit S. Aulakh

[57] ABSTRACT

A clear deodorant stick composition is disclosed that includes a solvent, a gelling agent, an odor-controlling agent selected from the group consisting of a germicidal agent, a deodorizing agent, a masking agent and a combination thereof, and a plasticizing/solubilizing agent selected from the group consisting of polyoxyethylene-polyoxypropylene 2-decyltetradecyl ether, ethoxylated dimethicone copolyol, and combinations thereof.

21 Claims, No Drawings

CLEAR STICK DEODORANT

The present invention relates generally to a composition that is useful as a stick deodorant. More particularly, this invention relates to a stick composition that provides deodorant protection when applied to the underarm region. The resulting composition is clear or translucent, and provides an enhanced payoff and feel on the skin.

BACKGROUND OF THE INVENTION

Stick deodorant compositions make up a large proportion of the personal anti-odor compositions now on the market. It has recently been discovered that stick deodorants that are clear or translucent (instead of opaque) are preferred by many consumers. Accordingly, a number of clear stick deodorant compositions have been developed. However, many of the known clear stick deodorant compositions suffer from certain limitations. Some compositions are unstable over time or under the extremes of temperature encountered during shipment and storage. Others cause an unpleasant stinging sensation when they are applied to the underarm area. Some such compositions produce sticks that are very hard, and do not have adequate payoff on the skin. Accordingly, a demand exists for a clear deodorant stick that does not have these drawbacks.

SUMMARY OF THE INVENTION

Against the foregoing background, it is a primary object of the present invention to provide a clear deodorant stick that has good payoff and feel on the skin.

It is another object of the present invention to provide such a clear deodorant stick that does not sting when applied to skin.

It is a still further object of the present invention to provide such a clear deodorant stick that is stable over time and under a wide range of temperatures.

It is a further object of the present invention to provide such a clear deodorant stick that is economical to manufacture.

To the accomplishment of the foregoing objects and advantages, the present invention, in brief summary, is a clear deodorant stick composition including a solvent, a gelling agent, an odor-controlling agent selected from the group consisting of a germicidal agent, a deodorizing agent, a masking agent and a combination thereof, and a plasticizing/solubilizing agent selected from the group consisting of polyoxyethylene-polyoxypropylene 2-decyltetradecyl ether, ethoxylated dimethicone copolyol, and combinations thereof.

DESCRIPTION OF THE PREFERRED EMBODIMENTS

The present invention provides a stick deodorant composition that is substantially transparent or translucent and that has a smooth, silky feel on contact with the skin. Moreover, the stick deodorant composition of the present invention provides a solid mass that is rigid enough to maintain its shape as a stick, but that is soft enough to provide good payoff of the product, and to deliver the active ingredient or ingredients to the underarm area. In addition, the stick deodorant is stable over time and under extreme temperature conditions, such as those encountered during shipping and storage. It resists syneresis better than most conventional clear deodorant sticks.

Clear stick deodorants according to the present invention preferably include a base having a solvent component. This solvent is preferably a C2 to C6 polyhydric alcohol, water, or a combination thereof. A polyhydric alcohol component serves also as an emollient. Most preferably, the solvent is a mixture of water and propylene glycol. The solvent is preferably present at about 70 to about 95 weight percent, with a range of about 70 to about 90 weight percent being more preferred. Of that component, water is preferably present at about 10 to about 20 weight percent.

The deodorants of the present invention also preferably include a gelling agent. This gelling agent is preferably a soap-type gelling agent, more preferably a sodium salt of fatty acids, and most preferably sodium stearate. It is also preferred that the sodium stearate be a mixture of two or more commercially available grades of sodium stearate. For enhanced stability, sodium stearate grade 1 and sodium stearate grade 2 preferably are combined. Sodium stearate grade 1 preferably contains about 30% minimum to about 41% maximum C20 and higher saturated chain length fatty acids. Most preferred is sodium stearate (OP-200) sold by RTD Chemicals. Sodium stearate grade 2 preferably contains about 88% minimum C16 and C18 fatty acids, and about 2% maximum fatty acids longer than C18. Most preferred is sodium stearate C-1 sold by Witco. This preferred mixture provides a superior balance of acceptable product odor, clarity and syneresis resistance. The gelling agent is preferably present at about 4 to about 10 weight percent, with a range of about 5 to about 8 weight percent being preferred.

It is preferred that the deodorant sticks of the present invention include a germicidal agent. Of the commercially available germicidal agents suitable for use in underarm deodorants, the most preferred is a trichlorohydroxy diphenyl ether sold under the tradename Triclosan. The germicidal agent is preferably present at less than about 2 weight percent.

In addition, or in the alternative, it is preferred that the deodorant sticks of the present invention include a fragrance or other deodorizing or masking agent. Most commercially available fragrances are suitable for use in the deodorant sticks of the present invention. Preferably, the fragrance is present at less than about 2 weight percent.

It has surprisingly been discovered that the addition of certain plasticizing/solubilizing agents to deodorant sticks having the foregoing ingredients allows the formation of a clear or translucent stick that avoids the limitations of the prior art. Most preferred of these plasticizing/solubilizing agents are the NIKKOL PEN series of solubilizers sold by Nikko Chemicals Co., Ltd. The PEN series includes various polyoxyethylene-polyoxypropylene 2-decyltetradecyl ethers, such as POE(12)POP(6) 2-decyltetradecyl ether, POE(20)POP(6) 2-decyltetradecyl ether, and POE(30)POP(6) 2-decyltetradecyl ether, which are sold as NIKKOL PEN-4612, PEN-4620 and PEN-4630 respectively. The CTFA adopted names for these compounds are PPG-6-decyltetradeceth-12, PPG-6-decyltetradeceth-20, and PPG-6-decyltetradeceth-30, respectively. Of these three, PEN-4620 is preferred for use. The use of this solubilizer in the clear deodorant sticks of the present invention is surprising. Chain lengths approaching C24 usually have decreased solubility in glycols/water. For example, beheneth-C22 clouds up equivalent clear stick compositions at cold temperatures. Nonetheless, PEN-4620 provides improved performance versus the shorter chain length of PEN-4612. For example, more than about 5 weight percent of PEN-4612 is needed to achieve the same clarity and stability of PEN-4620 used at 3.5 weight percent. The plasticizing agent is preferably present at about 1 to about 10 weight percent, more preferably at about 3 to about 8 weight percent, with about 3 to about 4 weight percent being most preferred.

Other plasticizers are also preferred for use in the deodorant sticks of the present invention. These plasticizers may be used in place of, or in addition to, the preferred PEN series solubilizers. Of these, the preferred plasticizer is an ethoxylated dimethicone copolyol. It is preferred that the ethoxylated dimethicone copolyol be present at about 2 to about 6 weight percent, with about 3.5 to about 4 weight percent being more preferred. Most preferred for use in the deodorant sticks of the present invention is Silicone Fluid SF1288, CTFA name Dimethicone Copolyol, available commercially from GE Silicones.

The use of an ethoxylated dimethicone copolyol is unexpected, because it is not usually seen as a beneficial or necessary ingredient in this context. Silicones are usually used to provide emolliency, slip or some conditioning benefit. These attributes would not be required in the deodorant sticks of the present invention because of the presence of a high percentage of propylene glycol. In addition, some other silicones do not work effectively as plasticizers in the deodorant sticks of the present invention because they are not soluble in the base of the present invention. For example, cetyl dimethicone copolyol, available commercially from Goldschmidt Chemical Corporation as ABIL EM 90, is not soluble in the base. Dow Corning's 749 Fluid, decamethyl cyclopentasiloxane (and) trimethylated silica, is likewise not soluble. Other silicones, while soluble, do not yield a stick of the same clarity as the preferred SF1288, or produce a somewhat less stable product. For example, General Electric's SF1188A and Dow Corning's 2501 Cosmetic Wax, both dimethicone copolyols, yielded sticks with greater syneresis than the preferred SF1288. A stick made with Dow Corning's 193 Surfactant, dimethyl siloxane/glycol copolymer, was more translucent with greater syneresis when compared to the SF1288 composition.

Other plasticizers that have been tried initially in the deodorant sticks of the present invention include PPG-1-isoceteth acetate and glycerol monooleate. Although initially acceptable, products made with these ingredients became nearly opaque within six months.

When the ethoxylated dimethicone copolyol plasticizer is used in deodorant sticks of the present invention, it is preferred that a PPG-10 butane diol component also be added to the composition. This butane diol acts to further enhance the high temperature stability of the formula, eliminating syneresis when sticks are stored at 110° F. for a month. In the alternative, propylene glycol can be used in place of the butane diol component. With the PEN plasticizers, a stability enhancing adjunct is not necessary. Preferably, this component is present at about 3 weight percent to about 10 weight percent, with 5 weight percent being more preferred.

The deodorant sticks of the present invention can also include adjunct ingredients such as emollients and colorants. Opacifying agents can also be added if a clear or translucent product is not desired.

Preferred Example 1

| Ingredient | Weight Percent |
| --- | --- |
| Propylene glycol-solvent | 69.185 |
| PPG-10 butane diol-solvent | 5.00 |
| Demineralized water-solvent | 15.00 |

-continued

| Ingredient | Weight Percent |
| --- | --- |
| Sodium stearate-gellant | 6.00 |
| Dimethicone copolyol-ws-ethoxylated-solubilizer/plasticizer | 3.50 |
| Trichlorohydroxy diphenyl ether-germicide | 0.30 |
| Fragrance | 1.00 |
| FD & C dyes | 0.015 |

Preferred Example 2

| Ingredient | Weight Percent |
| --- | --- |
| Propylene glycol-solvent | 74.185 |
| Demineralized water-solvent | 15.00 |
| Sodium stearate-gellant | 6.00 |
| PPC-6-decyltetradeceth-20-solubilizer/plasticizer | 3.50 |
| Trichlorohydroxy diphenyl ether-germicide | 0.30 |
| Fragrance | 1.00 |
| FD & C dyes | 0.015 |

The invention having been thus described with particular reference to the preferred forms thereof, it will be obvious that various changes and modifications may be made therein without departing from the spirit and scope of the invention as defined in the appended claims.

What is claimed is:

1. A clear deodorant stick composition comprising:
   a solvent;
   a gelling agent;
   an odor-controlling agent selected from the group consisting of a germicidal agent, a deodorizing agent, a masking agent, and a combination thereof; and
   a plasticizing/solubilizing agent containing polyoxyethylene-polyoxypropylene 2-decyltetradecyl ether.

2. The clear deodorant stick composition of claim 1, wherein said solvent is selected from the group consisting of a C2 to C6 polyhydric alcohol, water, and a combination thereof.

3. The clear deodorant stick composition of claim 1, wherein said solvent is a mixture of water and propylene glycol.

4. The clear deodorant stick composition of claim 1, wherein said solvent is present at about 70 to about 95 weight percent.

5. The clear deodorant stick composition of claim 1, wherein said solvent is present at about 70 to 90 weight percent.

6. The clear deodorant stick composition of claim 3, wherein said water is present at about 10 to about 20 weight percent.

7. The clear deodorant stick composition of claim 1, wherein said gelling agent is a soap-type gelling agent.

8. The clear deodorant stick composition of claim 7, wherein said gelling agent is a sodium salt of fatty acids.

9. The clear deodorant stick composition of claim 8, wherein said gelling agent is sodium stearate.

10. The clear deodorant stick composition of claim 8, wherein said gelling agent is a mixture of at least two commercially available grades of sodium stearate.

11. The clear deodorant stick composition of claim 1, wherein said gelling agent is present at about 4 to about 10 weight percent.

12. The clear deodorant stick composition of claim 1, wherein said gelling agent is present at about 5 to about 8 weight percent.

13. The clear deodorant stick composition of claim 1, wherein said odor-controlling agent is present at less than about 2 weight percent.

14. The clear deodorant stick composition of claim 1, wherein the odor-controlling agent is Triclosan.

15. The clear deodorant stick composition of claim 1, wherein said plasticizing/solubilizing agent is selected from the group consisting of NIKKOL PEN-4620, NIKKOL PEN-4612 and NIKKOL PEN-4630.

16. The clear deodorant stick composition of claim 1, wherein said plasticizing/solubilizing agent is NIKKOL PEN-4620.

17. The clear deodorant stick composition of claim 15, wherein said plasticizing/solubilizing agent is present at about 1 to about 10 weight percent.

18. The clear deodorant stick composition of claim 15, wherein said plasticizing/solubilizing agent is present at about 3 to about 8 weight percent.

19. The clear deodorant stick composition of claim 15, wherein said plasticizing/solubilizing agent is present at about 3.5 weight percent.

20. A method of deodorizing skin comprising applying to said skin a clear deodorant stick composition containing:

a solvent;

a gelling agent;

an odor-controlling agent selected from the group consisting of a germicidal agent, a deodorizing agent, a masking agent, and a combination thereof; and a plasticizing/solubilizing agent containing polyoxyethylene-polyoxypropylene 2-decyltetradecyl ether.

21. A clear deodorant stick composition comprising:

a solvent selected from the group consisting of a C2 to C6 polyhydric alcohol, water and a combination thereof;

a fatty acid salt gelling agent;

an odor-controlling agent selected from the group consisting of a germicidal agent, a deodorizing agent, a masking agent, and a combination thereof; and a plasticizing/solubilizing agent containing polyoxyethylene-polyoxypropylene 2-decyltetradecyl ether.

* * * * *